United States Patent [19]

Percy

[11] 4,247,487

[45] Jan. 27, 1981

[54] STABILIZED FORMALDEHYDE SOLUTIONS

[75] Inventor: James S. Percy, Wilmington, Del.

[73] Assignee: E. I. Du Pont de Nemours and Company, Wilmington, Del.

[21] Appl. No.: 318,462

[22] Filed: Dec. 26, 1972

[51] Int. Cl.$^3$ ............................................. C07C 47/04
[52] U.S. Cl. ..................................................... 568/422
[58] Field of Search ........................................ 260/606

[56] References Cited

U.S. PATENT DOCUMENTS

| | | | |
|---|---|---|---|
| 3,379,769 | 4/1968 | Prinz et al. ............................ | 260/606 |
| 3,658,912 | 4/1972 | Wambach et al. .................... | 260/606 |

FOREIGN PATENT DOCUMENTS

| | | | |
|---|---|---|---|
| 848787 | 9/1960 | United Kingdom ...................... | 260/606 |
| 968762 | 9/1964 | United Kingdom ...................... | 260/606 |

OTHER PUBLICATIONS

Kirk–Othmer, Encyclopedia of Chemical Technology, Second edition, John Wiley and Sons, Inc., New York, pp. 304–311 (1970).

*Primary Examiner*—Werren B. Lone

[57] ABSTRACT

Aqueous solutions of formaldehyde are stabilized against precipitation by the incorporation therein of 0.1 to 1000 p.p.m. of a low molecular weight vinyl polymer containing acetal, acetate, hydroxyl, and optionally, formal, propional or butyral groups. Preferably, the polymer is added to the formaldehyde solution as a methanol solution.

7 Claims, No Drawings

STABILIZED FORMALDEHYDE SOLUTIONS

BACKGROUND OF THE INVENTION

Aqueous solutions of over 30% by weight formaldehyde, e.g., 30 to 80% by weight solutions, tend to be unstable and as a result precipitate formaldehyde polymers. This is indicated by the solution becoming cloudy and/or formation of deposits.

The art is well aware of this problem and many solutions have been proposed. Thus, formaldehyde solutions have been stabilized by diluting the concentration of formaldehyde, keeping the solution at high temperatures, or adding a stabilizer. Stabilizers that have been used include methanol, urea, melamine, organic colloids, e.g., methyl cellulose, graft polymers of vinyl acetate and ethylene glycol formaldehyde polyacetal, water insoluble acetals of polyvinyl alcohol, and other polymeric materials, e.g., U.S. Pat. Nos. 3,406,206; 3,518,313; 3,658,912; 3,137,736; 3,379,769; German Pat. No. 1,963,524 and Japanese Pat. Publication No. 4109/1962.

The use of any of the above stabilizing materials has not resolved the stability problem to the complete satisfaction of formaldehyde users. Some of the materials do not provide the desired degree of stabilization, particularly at low temperatures and at relatively high concentrations of formaldehyde. Others are insoluble in formaldehyde to such an extent that other materials must be used in conjunction with them, e.g., U.S. Pat. No. 3,518,313 teaches the use of anionic surface active agents in combination with water insoluble polyvinyl acetal polymers. Accordingly, there is still a need for an improved stabilizer for formaldehyde solutions.

SUMMARY OF THE INVENTION

I have discovered that solutions of over 30% by weight of formaldehyde in water can be stabilized against precipitation by including therein, optionally but preferably in the form of a solution in methanol, a low molecular weight vinyl polymer, the polymer containing 1 to 40 mole percent of polyvinyl alcohol groups, 30 to 90 mole percent polyvinyl acetal type groups and 0 to 30 mole percent of polyvinyl acetate groups.

The polyvinyl acetal type groups of the polymer can be composed of acetal alone or of the acetal with formal, propional or butyral groups, depending upon the aldehyde present during preparation. Preferably, the acetal type groups are all acetal groups in view of the fact the resulting polymer is more soluble in formaldehyde.

The number average molecular weight of the polymer stabilizer can vary over the range of 300 to 5,000 but preferably is in the range of 1,000 to 3,000.

The polymers of the invention have the advantages that not only are they effective stabilizers, they also have a relatively high solubility in the formaldehyde, thus they are easier to incorporate in the formaldehyde.

PREPARATION OF THE STABILIZER

The polymer stabilizer of the invention can be prepared by a process which involves the polymerization of vinyl acetate, acid hydrolysis and/or methanolysis, acetalation, neutralization, and filtration steps. Alternatively, the polymer stabilizer can be made without the polymerization step if polyvinyl acetate of low molecular weight or low molecular weight polyvinyl alcohol is employed as a starting material.

The following paragraphs describe various processes for preparing the stabilizers.

A solution of vinyl acetate (e.g., a 5% solution in methanol) can be batch polymerized by heating to reflux (63°–66° C.) in the presence of an initiator, e.g., azobisisobutyronitrile, as conventionally practiced by those skilled in the art, e.g., 0.005 to 0.5% of the combined weight and vinyl acetate. This reaction is continued until the conversion to polyvinyl acetate is 35 to 60% complete, preferably 45 to 55%, based on dissolved solids and residual vinyl acetate. This generally takes about 10–20 hours. Additional initiator can be added if necessary and other initiators known in the art can be employed, e.g., benzoyl peroxide.

After this polymerization step, an acid catalyst or water and an acid catalyst, e.g., concentrated sulfuric acid (95–97%), can be added to the solution while it is still at reflux temperature. Sufficient acid is added to adjust the pH to below 3 and preferably to pH 1. The solution is then held at this temperature for a period of time to hydrolyze or methanolize any residual vinyl acetate, from the polyvinyl alcohol groups, begin the formation of polyvinyl acetal groups, and esterify the acetic acid by-product. The period of time can be about 30 minutes. Other acids can be employed, e.g., hydrochloric, formic, chloroacetic, perchloric, phosphoric or hydrobromic.

In the event it is desired to have polyvinyl formal groups present in the polymer stabilizer, formaldehyde in any convenient form (such as 37% formalin) can be added and the mixture held at reflux for 1–18 hours, generally about 7 hours. During this period of time, polyvinyl formal groups are formed and the reactions started during the acid addition continue. In a similar manner propional and butyral groups can also be added to the polymer by the addition of the appropriate aldehyde.

The solution is then neutralized, for example with 50% NaOH solution, and cooled to ambient temperatures. The neutralization can be accomplished with other neutralizing agents, e.g., alkali metal oxides or hydroxides or ammonium hydroxide, and if desirable, ion-exchange could be employed. The solution should be held for a period of time, i.e., at least 4 hours, while the precipitation of solids, e.g., $Na_2SO_4$ and $NaC_2H_3O_2$, occurs. The solids are then filtered off and the polymer solution is ready for use. If an ion exchange material is used, filtration is not necessary.

In an alternate process the polymerization step can be omitted if commercial low molecular weight, i.e., 500 to 5000 number average, polyvinyl acetate or polyvinyl alcohol dissolved in methanol is employed as a starting material.

Further, the formaldehyde or other aldehyde need not be added and the resulting polymer will not contain any polyvinyl formal, propional or butyral groups.

In another embodiment, acetaldehyde or vinyl acetate can be added with the water and acid to the polyvinyl acetate and the resulting mixture held at reflux for several hours. In use of these materials are equivalent as the vinyl acetate decomposes to acetaldehyde and acetic acid in the presence of water. The acetaldehyde then reacts with the polymer to form the polyvinyl acetal groups.

The vinyl acetate or acetaldehyde is added to insure that sufficient acetaldehyde is available during the acetalation process. Thus, when polyvinyl acetate or polyvinyl alcohol is the starting material, these materials must be added. These materials should be added to insure that there will be at least 1.1 moles of acetaldehyde after the hydrolysis for each two moles of vinyl acetate converted to polymer.

It is convenient to run the above reactions in methanol, as methanol is a solvent for the polymer and it can be added with the polymer to the formaldehyde without creating any contaminants in the formaldehyde. However, the reactions can be conducted in other solvents, e.g., ethanol, acetone, methyl acetate, or methyl formate.

An advantage of these processes is that a single vessel can be used for all the steps and the product solution can be utilized directly.

The above processes will be described in detail in the Examples.

THE POLYMER STABILIZER

The polymer stabilizers of the invention have not been completely characterized; however, the following properties are known.

The polymer will have a number average molecular weight between 300 and 5,000 and preferably between 1,000 and 3,000. These molecular weights are measured by vapor pressure osmometry.

It is desirable to have the molecular weight in the claim range as polymers having higher molecular weights are insoluble and of lower molecular weight are not as effective as stabilizers.

The polymer will have the following composition:
polyvinyl acetal type groups of 30–90 mole percent
polyvinyl alcohol of 1–40 mole percent
polyvinyl acetate of 0–30 mole percent
these compositions can be determined by infrared spectroscopy.

The polyvinyl acetal type portion of the polymer is composed of acetal or acetal with formal, propional and butyral groups or mixtures thereof. The amount of acetal type groups present in each polymer depends on whether the solutions contained the appropriate aldehyde. Thus, if only acetaldehyde is present, the polymer will contain only polyvinyl acetal groups. Polymers having an acetal type group content below 30 mole percent may still stabilize formaldehyde solutions but they are not as effective.

The polyvinyl acetate group will be present in an amount depending on how far the alcoholysis has progressed. If the reaction is continued long enough, the acetate content can be reduced to essentially zero. The acetate groups may aid in the solubility, but they are not as effective as acetal groups in stabilizing formaldehyde. Accordingly, it is preferred that they be present in amounts of 0 to 10%.

At equilibrium, hydroxyl groups in the form of polyvinyl alcohol will always be present in the polymer.

As previously set forth it is preferred to prepare the polymer stabilizer in methanol and use it as a solution in methanol. However, the polymer can be dissolved in other solvents and added to the formaldehyde. Examples of other solvents include ethanol and water.

The stabilizer solution should have a neutral pH to avoid acid or base catalyzed reactions of formaldehyde. Thus, a solution pH of 7.0–8.0, preferably 7.5, as measured directly by a pH meter on the methanolic solution is found to be useful.

USE OF THE STABILIZER

The polymer stabilizer can be added to formaldehyde as such, or preferably as a solution in a solvent, e.g., methanol.

The amount of polymer stabilizer added to the aqueous formaldehyde solution will depend upon the strength of the solution and normally ranges from 1 to 100 p.p.m. (of the polymer). Thus, with a 50% formaldehyde solution 10 p.p.m. can be employed with greater or lesser quantities in higher or lower strength formaldehyde.

The polymer stabilizer, particularly when in a methanol solution, is miscible with the formaldehyde; at the concentrations of interest thus, the addition is not difficult. However, the stabilizer should be evenly distributed throughout the formaldehyde batch being stabilized; thus, means to obtain thorough mixing should be employed, e.g., agitation.

The following Examples are offered to illustrate the invention; all parts are parts by weight unless otherwise indicated.

EXAMPLE 1

Polymerization

To 500 parts of vinyl acetate in 9500 parts of methanol is added 5 parts of azobisisobutyronitrile. The mixture is heated to reflux (65° C.) for 18 hours with agitation.

Hydrolysis-Acetalation

The polymerization step product is cooled to 62° C., and 1000 parts of water (ambient temperature) and 364 parts of concentrated sulfuric acid are added. The mixture is held for 30 minutes at about 60° C. while the hydrolysis of the residual vinyl acetate occurs and the acetalation begins.

Formalation

To this solution is then added 540 parts of a 37% formaldehyde solution in water (this formaldehyde contains 12–15% methanol). The mixture is refluxed for six hours and then cooled to 45° C.

Neutralization-Filtration

The solution is neutralized to pH 7.5 with 411 parts of a 50% NaOH solution. The solution is then allowed to cool to ambient temperature and agitated for 15 hours. As the last preparation step the precipitated sodium sulfate, sodium acetate and insoluble polymer are removed by filtration. A clear solution is obtained that is miscible with aqueous formaldehyde at the concentration of interest.

UTILITY

The solution was mixed with unstabilized 50% aqueous formaldehyde in the following ratios and held at 40° C. until a white formaldehyde polymer precipitated.

| PARTS BY VOLUME STABILIZER SOLUTION: UNSTABILIZED 50% CH$_2$O | DAYS STABILITY AT 40° C. |
| --- | --- |
| 0:1 | less than ONE |
| 1:163 | more than 90 |
| 1:1630 | 42 |
| 1:16300 | 17 |

EXAMPLE 2

Polymerization

To 100 parts of vinyl acetate in 900 parts of methanol is added 0.5 part of azobisisobutyronitrile. The mixture is heated to reflux for 7 hours.

Hydrolysis-Acetalation

The mixture is cooled to ambient temperature and 100 parts of water at ambient temperature is added. Then 37 parts of concentrated $H_2SO_4$ is added and the mixture refluxed for 6½ hours.

Neutralization-Filtration

The mixture is cooled to ambient and neutralized to pH 7.5 with 50% NaOH solution. The mixture is allowed to settle for 15 hours and the white precipitate is removed by filtration.

UTILITY

The clear solution was mixed with unstabilized 50% formaldehyde in the following ratios and held at 40° C. until a white formaldehyde polymer precipitated.

| PARTS BY VOLUME STABILIZER SOLUTION: UNSTABILIZED 50% $CH_2O$ | DAYS STABILITY AT 40° C. |
|---|---|
| 1:400 | 64 |
| 1:4000 | 64 |
| 1:40000 | 9 |

EXAMPLE 3

4.5 parts of a low molecular weight polyvinyl acetate ("Gelva" V1.5, $Mw_n$ 4400) is dissolved in 85 parts of methanol.

To this solution is added 2.3 parts of acetaldehyde, 1.8 parts of water and 3.3 parts of concentrated sulfuric acid. The mixture is refluxed 7 hours, cooled to ambient, neutralized to pH 7.5 with NaOH and filtered.

The resulting polymer in methanol is useful to stabilize aqueous formaldehyde solutions.

Instead of the polyvinyl acetate above, 2.3 parts of a low molecular weight polyvinyl alcohol could also be employed with similar results.

EXAMPLE 4

Five parts of a commercial, low molecular weight polyvinyl acetate ("Gelva" V1.5 manufactured by Monsanto and having a number average molecular weight of 4,400) in 95 parts of methanol is heated to reflux. To this solution is added 5 parts of vinyl acetate or 2.6 parts of acetaldehyde, 2 parts by volume of concentrated sulfuric acid and 2 parts by volume of water. The mixture is held at reflux for 7 hours, neutralized to pH 7.5 with 50% sodium hydroxide solution and the settled solids filtered off.

The resulting solution (2.6% solution of the polymer in methanol) can be used to stabilize aqueous solutions of formaldehyde.

I claim:

1. A stabilized solution of over 30% by weight of formaldehyde in water containing a stabilizing amount of a formaldehyde-soluble polymer having a number average molecular weight of 300–5000 prepared by acetalization of polyvinyl alcohol with a $C_{1-4}$ alkyl aldehyde, the polymer containing along the polymer chain 30–90% acetal groups, 1–40% hydroxyl groups and 0–30% acetate groups.

2. The solution of claim 1 wherein the stabilizing amount ranges from 0.1 to 1000 p.p.m.

3. The solution of claim 1 wherein the stabilizing amount ranges from 1 to 100 p.p.m.

4. A stabilized solution of over 30% by weight of formaldehyde in water containing 1 to 100 p.p.m. of a vinyl polymer in methanol, said polymer having a number average molecular weight of 300–5000 and being made by (1) polymerizing vinyl acetate in solution in methanol in the presence of azobisisobutyronitrile as an initiator at reflux until 35 to 60% of the vinyl acetate is converted to polyvinyl acetate, then (2) adding water and sulfuric acid while the solution is at reflux and holding at reflux for 30 minutes, thereafter (3) adding a formaldehyde solution and holding the solution at reflux for 6 to 7 hours and then (4) neutralizing with sodium hydroxide and filtering to remove settled solids.

5. A stabilized solution of over 30% by weight of formaldehyde in water containing 1 to 100 p.p.m. of a vinyl polymer in methanol, said polymer having a number average molecular weight of 300–5000 and being made by (1) polymerizing vinyl acetate in solution in methanol in the presence of azobisisobutyronitrile as an initiator at reflux until 35 to 60% of the vinyl acetate is converted to polyvinyl acetate, then (2) adding water and sulfuric acid while the solution is at reflux and holding at reflux for 6 to 7 hours and then (3) neutralizing with sodium hydroxide and filtering to remove settled solids.

6. A stabilized solution of over 30% by weight of formaldehyde in water containing 1 to 100 p.p.m. of a vinyl polymer in methanol, said polymer being made by dissolving a polyvinyl acetate, having a number average molecular weight of 300–5000, in methanol, heating to reflux and adding vinyl acetate or acetaldehyde, concentrated sulfuric acid, and water and holding at reflux for 6 to 7 hours, and then neutralizing with sodium hydroxide and filtering to remove settled solids.

7. A stabilized solution of over 30% by weight of formaldehyde in water containing 1 to 100 p.p.m. of a vinyl polymer in methanol, said polymer being made by dissolving a polyvinyl alcohol, having a number average molecular weight of 300–5000, in methanol, heating to reflux and adding vinyl acetate or acetaldehyde, concentrated sulfuric acid, and water and holding at reflux for 6 to 7 hours, and then neutralizing with sodium hydroxide and filtering to remove settled solids.

* * * * *